United States Patent [19]

Rösner et al.

[11] Patent Number: 4,782,056
[45] Date of Patent: * Nov. 1, 1988

[54] 2-PHENYLHEXAHYDRO-1,2,4-TRIAZINE-3,5-DIONES

[75] Inventors: Manfred Rösner, Eppstein; Wolfgang Raether, Dreieich, both of Fed. Rep. of Germany

[73] Assignee: Hoechst Aktiengesellschaft, Frankfurt, Fed. Rep. of Germany

[*] Notice: The portion of the term of this patent subsequent to Feb. 3, 2004 has been disclaimed.

[21] Appl. No.: 903,752

[22] Filed: Sep. 5, 1986

[30] Foreign Application Priority Data

Sep. 7, 1985 [DE] Fed. Rep. of Germany ....... 3531919

[51] Int. Cl.[4] .................... A61K 31/53; C07D 253/06
[52] U.S. Cl. .................... 514/242; 544/182; 544/112; 544/58.5; 544/83; 514/227.8; 514/236.2
[58] Field of Search ............... 514/242, 222, 232, 230, 514/228, 234, 237, 238; 544/182, 58.5, 112, 83

[56] References Cited

U.S. PATENT DOCUMENTS

| | | | |
|---|---|---|---|
| 4,198,407 | 4/1980 | Rosner et al. | 424/249 |
| 4,426,522 | 1/1984 | Simonovitch | 544/182 |
| 4,640,917 | 2/1987 | Rosner et al. | 544/182 |

FOREIGN PATENT DOCUMENTS

| | | |
|---|---|---|
| 0058534 | 8/1982 | European Pat. Off. . |
| 2423972 | 1/1975 | Fed. Rep. of Germany . |

Primary Examiner—John M. Ford
Attorney, Agent, or Firm—Finnegan, Henderson, Farabow, Garrett and Dunner

[57] ABSTRACT

Compounds of the formula I

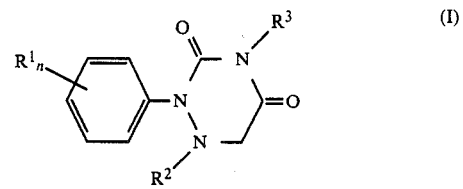

with n=1-3, R=H, Hal, $CF_3$, alkyl, cycloalkyl, alkyloxy, alkylthio, alkylsulfinyl, alkylsulfonyl, benzylsulfinyl, benzylsulfonyl, nitro, cyano, amino, alkylamino, dialkylamino, piperidino, morpholino, pyrrolidinyl, 4-methyl-1-piperazinyl, acylamino or substituted phenoxy, phenylthio, phenylsulfinyl, phenylsulfonyl, benzoyl, benzoylamino or anilino, with $R^2$=H, alkyl, cycloalkyl, optionally substituted benzyl, alkanoyl or benzoyl and $R^3$=H, alkyl, cycloalkyl or optionally substituted benzyl, at least $R^2$ or $R^3$ not being H, are obtained by alkylation or acylation of a compound II

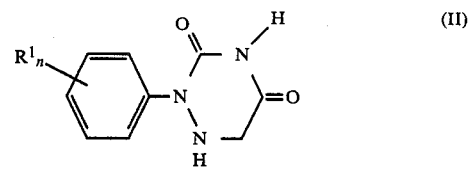

in which $R^1$ is as defined above, with compounds $R^3X$ (X=leaving group) or $R^2Y$ (Y=leaving group), $R^2$ and $R^3$ being defined as indicated.

Compounds I are coccidiostatics.

6 Claims, No Drawings

2-PHENYLHEXAHYDRO-1,2,4-TRIAZINE-3-,5-DIONES 1,2,4-Triazine-3,5-(2H,4H)-diones having coccidiostatic activity, and their preparation, are disclosed in, inter alia, German Offenlegungsschrift No. 2,722,537 which is equivalent to U.S. Pat. No. 4,198,407. Hexahydro-1,2,4-triazine-3,5-diones having a benzyl or thienylmethyl substituent in the 2-position are described in European patent application No. 58,534. Their coccidiostatic activities, however, are not satisfactory.

The object of the invention are therefore 2-phenylhexahydro-1,2,4-triazine-3,5-diones of the formula I or their salts

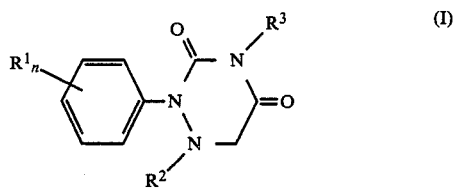 (I)

in which:

n denotes one, two or three and the individual substituents $R^1$, independently of one another, denote
(a) hydrogen, F, Cl, Br, I, trifluoromethyl, alkyl having 1 to 6 carbon atoms, cycloalkyl having 3 to 6 carbon atoms, alkoxy, alkylthio, alkylsulfinyl or alkylsulfonyl, each having 1 to 6 carbon atoms in the alkyl radical, benzylthio, benzylsulfinyl or benzylsulfonyl, nitro, cyano, amino, alkylamino or dialkylamino, each having 1 to 12 carbon atoms in the alkyl radical, piperidino, morpholino, thiomorpholino, 1-pyrrolidinyl, 4-methyl-1-piperazinyl, acylamino having 1 to 6 carbon atoms in the acyl radical, or
(b) a phenoxy, phenylthio, phenylsulfinyl, phenylsulfonyl, benzoyl, benzoylamino or anilino radical, each of which is substituted once, twice or three times by one of the substituents mentioned under (a);

$R^2$ denotes hydrogen, straight-chain or branched alkyl having 1 to 12 carbon atoms, cycloalkyl having 3 to 7 carbon atoms, benzyl which is unsubstituted or substituted by F, Cl, Br or ($C_1$-$C_4$)-alkyl, straight-chain or branched alkanoyl which has 1 to 12 carbon atoms and is unsubstituted or substituted once, twice or three times by F, Cl or Br, or benzoyl which is unsubstituted or substituted once or twice by F, Cl, Br or ($C_1$-$C_4$)alkyl;

$R^3$ denotes hydrogen, straight-chain or branched alkyl having 1 to 12 carbon atoms, cycloalkyl having 3 to 7 carbon atoms, or benzyl which is unsubstituted or substituted by F, Cl, Br or ($C_1$-$C_4$)alkyl, with the proviso that at least one of the radicals $R^2$ and $R^3$ is not hydrogen. In case if $R^3$ denotes hydrogen the compounds of formula I can form salts. The invention refers to such salts which are physiologically tolerable especially to the alkali metal, alkaline earth metal or ammonium salts.

Preferred compounds of the formula I are those in which one or more substituents have the following meaning:

n is two or three, and the individual substituents $R^1$, independently of one another, are
(c) hydrogen, fluorine, chlorine, bromine, trifluoromethyl, alkyl, alkoxy, alkylthio, alkylsulfinyl or alkylsulfonyl, each having 1 to 6 carbon atoms in the alkyl radical, or
(d) a phenoxy, phenylthio, phenylsulfinyl or phenylsulfonyl radical, each of which is substituted once or twice by one of the substituents mentioned under (c), $R^2$ is hydrogen, straight-chain or branched alkyl or alkanoyl, each having 1 to 4 carbon atoms, cycloalkyl having 3 to 7 carbon atoms, benzyl or benzoyl which both are unsubstituted or substituted by F, Cl, Br or ($C_1$-$C_4$)-alkyl;

$R^3$ is hydrogen, straight-chain or branched alkyl having 1 to 12 carbon atoms, cycloalkyl having 3 to 7 carbon atoms or benzyl which is unsubstituted or substituted by F, Cl, Br or ($C_1$-$C_4$)-alkyl;

with the proviso that at least one of the radicals $R^2$ and $R^3$ is not hydrogen, and their alkali metal, alkalineearth metal or ammonium salts where $R^3$ denotes hydrogen.

Very particularly preferred compounds of the formula I are those in which one or more substituents have the following meanings:

n is two or three, and the individual substituents $R^1$, independently of one another, are hydrogen, chlorine, trifluoromethyl, ($C_1$-$C_4$)-alkyl or phenoxy, which is substituted once or twice by alkylthio, alkylsulfinyl or alkylsulfonyl, each having 1 to 4 carbon atoms in the alkyl radical, or $R^2$ is ($C_1$-$C_4$)alkyl, ($C_1$-$C_4$)alkanoyl or benzyl, $R^3$ is hydrogen, ($C_1$-$C_4$)alkyl or benzyl;

and in which preferably the phenyl radical in formula I is disubstituted in the 3,5-positions or trisubstituted in the 3,4,5-positions.

The invention also relates to a process for the preparation of substituted hexahydro-1,2,4-triazine-3,5-diones of the formula I, which comprises alkylation or acylation of a hexahydro-1,2,4-triazine-3,5-dione of the formula II

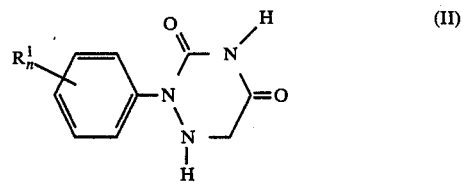 (II)

in which n and $R^1$ have the meanings indicated for formula I.

The compounds of the formula II are obtained by selective hydrogenation of the C-N double bond in compounds of the formula III

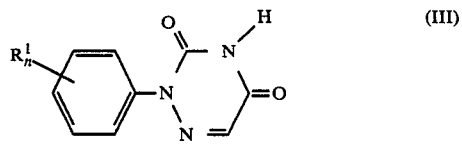 (III)

in which n and $R^1$ have the meanings indicated for formula I.

The reduction of the compounds of the formula III is carried out by generally known processes. Depending on the nature of the compound of the formula II, it can be carried out by catalytically activated hydrogen with catalysts such as Raney nickel, platinum, palladium, platinum(IV) oxide or by chemical reduction with metals, metal salts, metal carbonyls or complex hydrides. Examples which may be mentioned are sodium amalgam in ethanol, lithium in ammonia, tin(II) chloride in hydrochloric acid, iron in glacial acetic acid, lithium aluminum hydride, sodium borohydride, and sodium cyanoborohydride. The reduction is preferably carried out with zinc in glacial acetic acid or tin(II) chloride in hydrochloric acid, where appropriate in an inert solvent or diluent, such as methanol, ethanol, toluene, acetone, butanone, dimethoxyethane, tetrahydrofuran, dioxane, ethyl acetate, pyridine or glacial acetic acid.

The temperature used is, for example, from about 50° C. to 150° C., preferably between 80° C. and 120° C., or at the boiling point of the solvent or mixture of solvents used.

The processes for the preparation of compounds of the formula III are known from the literature.

The preparation is carried out by, for example, diazotization of an appropriately substituted aniline derivative and coupling of the diazonium salt with N,N'-bis(ethoxycarbonyl)malonamide, following by cyclization, hydrolysis and decarboxylation.

The preparation of compounds of the formula I in which $R^3$ does not denote hydrogen is carried out by generally known methods, using a base such as sodium hydride, sodium hydroxide or triethylamine and an alkylating agent of the formula IV

$$R^3-X \qquad (IV)$$

in which $R^3$ has the meanings indicated for formula I, with the exception of hydrogen, and X denotes a leaving group such as, for example, Cl, Br, I, tosylate or mesylate.

The preparation of compounds of the formula I in which $R^2$ does not denote hydrogen is carried out by reaction of a compound of the formula II with an alkylating or acylating agent of the formula V

$$R^2-Y \qquad (V)$$

in which $R^2$ has the meanings indicated for formula I, with the exception of hydrogen, and Y denotes a leaving group such as Cl, Br, I and, in the case of an alkylation, also tosylate or mesylate and, in the case of an acylation, also -O-alkanoyl.

The alkylation with a compound of the formula V is carried out without or, advantageously, with an inert solvent such as, for example, toluene, xylene, dimethylformamide, dimethyl sulfoxide, dimethyl sulfone, N-methylpyrrolidone, or mixtures thereof, by heating with the alkylating agent to, for example, 100°–250° C. under atmospheric pressure or in an autoclave. The reaction times for this are, for example, between 2 and 50 h.

The acylation of a compound of the formula V is carried out with or without solvent or diluent, preferably in an excess of the acylating agent, with or without catalyst. Suitable examples of the latter are concentrated sulfuric acid, as well as acid chlorides such as, for example, acetyl chloride, propionyl chloride, ethyl chloroformate, thionyl chloride or phosphorus oxychloride, which activate the intended acylating agent in a suitable manner. The reaction can be carried out in, for example, a temperature range from −20° to +150° C., preferably at 0° to 80° C. Depending on the reaction conditions employed, the reaction times may be between 30 minutes and 24 hours.

When, in the manner described above, compounds of the formula I in which $R^3$ denotes hydrogen are obtained, these can be converted into compounds of the formula I with $R^3$ not being hydrogen by generally known methods, using a base such as sodium hydride, sodium hydroxide or triethylamine and an alkylating agent of the formula IV.

In the case of the synthesis of a compound of the formula I in which $R^2$ and $R^3$ denote the same alkyl radical, it is possible, as selected, to carry out a stepwise or a simultaneous introduction of the two identical alkyl radicals using a combination of the reaction conditions described above. For example, this synthesis is carried out in an inert solvent, such as N-methylpyrrolidone, with an excess of the alkylating agent in the presence of a base, such as sodium hydride, at 100°–250° C., and under atmospheric pressure or in an autoclave.

The compounds of the formula I in which $R^3$ denotes hydrogen can be converted into the corresponding salts by the addition of, advantageously, one mole-equivalent of alkali, alkaline earth, ammonia or amines.

Preferably used for this purpose are sodium hydroxide, sodium methylate, sodium hydride, potassium hydroxide, calcium hydroxide, calcium hydride, ammonia, alkylamines, alkylene derivatives or alkanolamines such as, for example, ethanolamine.

The compounds of the formula I, according to the invention, are chemotherapeutic agents which can be used for protozoal diseases, and in particular as Coccidiostatics.

In poultry management, coccidiosis causes mortality and thus great economic losses. Prophylactic and therapeutic measures are thus necessary. Prophylaxis is of major importance, especially the administration with the feed of coccidiostatics, which prevents an outbreak of coccidiosis. In addition, these agents can also be used therapeutically for preexistent coccidiosis.

A coccidiostatic must display satisfactory activity against various species of Coccidia in low use concentrations, good tolerability and, resulting therefrom, a wide therapeutic range. In addition, new coccidiostatics should be active against strains of Coccidia which are already resistant to drugs.

Even very low amounts of compounds of the formula I, and their salts, display a pronounced effect on various organisms causing coccidiosis in poultry and other species of livestock with, at the same time, very good tolerability. Furthermore, they have an effect on organisms causing coccidiosis which display multiple drug-resistance.

In principle, the compounds of the formula I can be administered as the pure substance. They are preferably used in a mixture with a suitable vehicle. The salts are especially suitable for use in drinking water.

The customary feedstuff mixtures can be used as vehicle. This entails admixture of an active compound of the formula I at a concentration of 0.1–300 ppm, preferably 0.5–50 ppm, to the feed. Compared with the known aralkylhexahydrotriazines of European Pat. No. 58,534, which are effective only in the range from 70 to 200 ppm in the feed or drinking water, the compounds of the formula I, according to the invention, and their salts are especially distinguished by their efficacy in the low concentrations which have been indicated with, at the same time, good tolerability.

Furthermore, the compounds I are distinguished by high stability, especially towards light and air.

"Alkali metals" is intended to mean Li, Na or K, preferably Na or K. "Alkaline earth metals" is intended to mean Ca or Mg. Ammonium comprises not only $NH_4+$ but also compounds in which 1-4 hydrogen atoms have been replaced by, for example, alkyl, alkoxyalkyl, hydroxyalkyl, aminoalkyl or phenylalkyl with, in each case, 1-24 carbon atoms in the alkyl radical, or phenyl. It has been found that the compounds I have no mutagenic effect in the Ames test.

A. CHEMICAL EXAMPLES

Example 1

2-[3,5-Dichloro-4-(4-methylsulfonylphenoxy)phenyl]-1-methylhexahydro-1,2,4-triazine-3,5-dione 1 g of 2-[3,5-dichloro-4-(4-methylsulfonylphenoxy)-phenyl]hexahydro-1,2,4-triazine-3,5-dione in 10 ml of N-methylpyrrolidone was heated at 140° to 160° C. with 10 ml of methyl iodide for four hours and, after addition of a further 10 ml of methyl iodide, for a further three hours. After the mixture had been cooled, water was added and an oil separated out, which slowly became solid and was recrystallized from methanol with the addition of active charcoal. Melting point 223° C.

NMR spectrum, 270 MHz, DMSO-$d_6$, TMS as internal standard, δ values in ppm: —$N^1$—$\underline{CH_3}$ 2.7 (s), —$N^1$—$\underline{CH_2}$ 3.9 (s).

In an analogous procedure, the following compounds of the formula I additionally alkylated in the 1-position were obtained by alkylation from the particular 2-substituted hexahydro-1,2,4-triazine-3,5-diones:

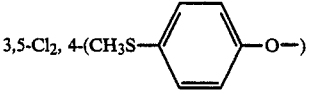
(I)

| EXAMPLE NO. | $R^1_n$ | $R^2$ | $R^3$ | mp. °C. |
|---|---|---|---|---|
| 2 | 3,5-Cl$_2$, 4-(CH$_3$S—⌬—O—) | CH$_3$ | H | 204 |
| 3 | 3,5-Cl$_2$, 4-(CH$_3$SO—⌬—O—) | CH$_3$ | H | 228 |
| 4 | 3,5-Cl$_2$, 4-(CH$_3$SO$_2$—⌬—O—) | ⌬—CH$_2$ | H | 228 |
| 5 | 3,5-Cl$_2$, 4(—⌬—CH$_2$S—⌬—O—) | ⌬—CH$_2$ | H | 178 |
| 6 | 3,5-Cl$_2$, 4-(CH$_3$S—⌬(CH$_3$)—O—) | CH$_3$ | H | 226 |
| 7 | 3,5-Cl$_2$, 4-(Cl—⌬—S—) | CH$_3$ | H | 195 |
| 8 | 3-Cl, 4-(CH$_3$S—⌬—O—) | CH$_3$ | H | |

-continued $$(I)$$

| EXAMPLE NO. | $R^1_n$ | $R^2$ | $R^3$ | mp. °C. |
|---|---|---|---|---|
| 9 | 3,5-(CH₃)₂, 4-(CH₃S—⟨phenyl⟩—O—) | CH₃ | H | |
| 10 | CH₃, 4-(CH₃S—⟨phenyl⟩—O—) | CH₃ | H | 151 |
| 11 | 4-(⟨phenyl⟩—S—) | CH₃ | H | 153 |
| 12 | 4-(CH₃S—⟨phenyl⟩—S—) | CH₃ | H | 170 |
| 13 | 3,5-Cl₂, 4-(CH₃S—⟨phenyl⟩—S—) | CH₃ | H | |
| 14 | 3,5-Cl₂, 4-CH₃S | CH₃ | H | 266 |
| 15 | 3,5-(CF₃)₂ | CH₃ | H | 143 |

Example 16

1-Acetyl-2-[3,5-dichloro-4-(4-methylsulfonylphenoxy)-phenyl]hexahydro-1,2,4-triazine-3,5-dione 2 g of 2-[3,5-dichloro-4-(4-methylsulfonylphenoxy)-phenyl]hexahydro-1,2,4-triazine-3,5-dione were suspended in 10 ml of acetic anhydride. 1 ml of concentrated sulfuric acid was added dropwise, during which there was a slight increase in the temperature of the suspension and the starting material slowly dissolved. The mixture was then stirred at room temperature for 2 to 3 hours, and was subsequently stirred with water. The product was filtered off with suction, washed with water and dried, and recrystallized from a little glacial acetic acid, melting point 267° C.

NMR spectrum, 60 MHz, DMSO-d₆, TMS as internal standard, δ values in ppm: —N¹—COCH₃ 2.1 (s), —N-1—CH₂ 4.6 (broad d, AB signal).

In an analogous procedure, the following compounds of the formula I additionally acylated in the 1-position were obtained by acylation from the particular 2-substituted hexahydro-1,2,4-triazine-3,5-diones:

| EXAMPLE NO. | $R^1_n$ | $R^2$ | $R^3$ | mp. °C. |
|---|---|---|---|---|
| 17 | 3,5-Cl₂,4-(CH₃S—⟨phenyl⟩—O—) | CH₃CO | H | 255 |
| 18 | 3,5-Cl₂,4-(CH₃SO₂—⟨phenyl⟩—O—) | C₂H₅CO | H | 238 |
| 19 | 3,5-Cl₂,4-(CH₃S—⟨phenyl⟩—O—) | C₂H₅CO | H | 179 |
| 20 | 3,5-(CF₃)₂ | CH₃CO | H | 170 |
| 21 | 3,5-(CF₃)₂ | C₂H₅CO | H | |
| 21a | 3,5-Cl₂,4-(CH₃—⟨phenyl⟩—O—) | C₆H₅CO | H | 217 |

Example 22

2-[3,5-Dichloro-4-(4-methylsulfonylphenoxy)phenyl]-1-formylhexahydro-1,2,4-triazine-3,5-dione 1 g of 2-[3,5-dichloro-4-(4-methylsulfonylphenoxy)-phenyl]hexahydro-1,2,4-triazine-3,5-dione was suspended in 10 ml of formic acid. 5 ml of propionyl chloride and 1 ml of concentrated sulfuric acid were successively added dropwise, and the mixture was stirred at 80° C. for 5 hours. After it had been cooled, a further 10 ml of propionyl chloride were added to complete the reaction, and the mixture was again heated at 80° C. for 5 hours with stirring. It was then poured onto ice-water, and the precipitate was filtered off with suction and extracted by boiling with a little toluene. The residue was recrystallized from isopropanol/diisopropyl ether, melting point 212° C., decomposition.

NMR spectrum, 60 MHz, DMSO-$d_6$, TMS as internal standard, δ values in ppm: —$N^1$—$\underline{CHO}$ 8.7 (s), —$N^2$—$\underline{CH_2}$ 4.8 (s)

The following was obtained analogously:

Example 23

2-[3,5-Dichloro-4-(4-methylthiophenoxy)phenyl]-1-formylhexahydro-1,2,4-triazine-3,5-dione, melting point 180°, decomposition.

Example 24

2-[3,5-Dichloro-4-(4-methylthiophenoxy)phenyl]-1,4-dimethylhexahydro-1,2,4-triazine-3,5-dione 0.7 g of 2-[3,5-dichloro-4-(4-methylthiophenoxy)-phenyl]-1-methylhexahydro-1,2,4-triazine-3,5-dione (Example 2) was dissolved in 5 ml of cold dimethylformamide. About 200 mg of a suspension (about 50%) of sodium hydride were added and, when evolution of gases was complete, 1 ml of methyl iodide was added dropwise, and the mixture was stirred at room temperature for 4 hours. After acidification with 2N HCl, extraction with methylene chloride and evaporation were carried out, and the remaining oil was triturated with petroleum ether, whereupon it crystallized; melting point 148° C. after recrystallization from isopropanol.

NMR spectrum, 60 MHz, DMSO-$d_6$, TMS as internal standard, δ values in ppm: —$N^1$—$\underline{CH_3}$ 2.7 (s), —$N^4$—$\underline{CH_3}$ 3.1 (s), —$N^1$—$\underline{CH_2}$ 4.0 (s).

In an analogous procedure, the following compounds of the formula I additionally alkylated in the 4-position were obtained by alkylation from the particular 1,2-disubstituted hexahydro-1,2,4-triazine-3,5-diones:

| EXAMPLE NO. | $R^1_n$ | $R^2$ | $R^3$ | mp. °C. |
|---|---|---|---|---|
| 25 | 3,5-Cl$_2$, 4-(CH$_3$SO$_2$—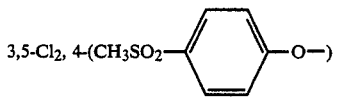—O—) | CH$_3$ | CH$_3$ | 178 |
| 26 | 3,5-Cl$_2$, 4-(CH$_3$SO$_2$—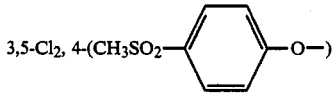—O—) | CH$_3$ | C$_2$H$_5$ | 181 |
| 27 | 3,5-Cl$_2$, 4-(CH$_3$S—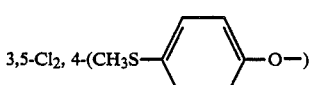—O—) | CH$_3$ | C$_2$H$_5$ | |
| 28 | 3,5-Cl$_2$, 4-(CH$_3$SO—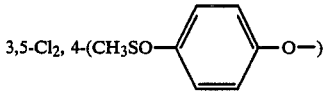—O—) | CH$_3$ | CH$_3$ | |
| 29 | 3,5-Cl$_2$, 4-(CH$_3$SO—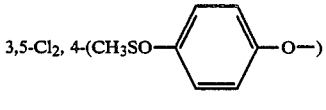—O—) | CH$_3$ | C$_2$H$_5$ | |
| 30 | 3,5-Cl$_2$, 4-(CH$_3$SO$_2$—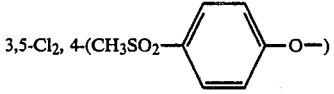—O—) | CH$_3$ | C$_4$H$_9$ | |
| 31 | 3,5-Cl$_2$, 4-(CH$_3$SO$_2$—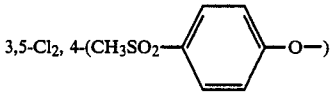—O—) | CH$_3$ | CH$_2$—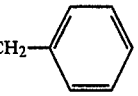 | 201 |
| 32 | 3,5-Cl$_2$, 4-(CH$_3$SO$_2$—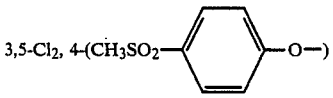—O—) | CH$_2$—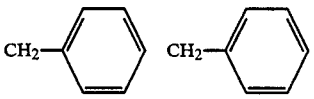 | CH$_2$—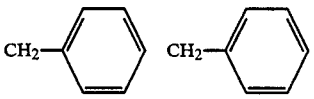 | |

-continued

| EXAMPLE NO. | $R^1_n$ | $R^2$ | $R^3$ | mp. °C. |
|---|---|---|---|---|
| 33 | 3,5-Cl$_2$, 4-(CH$_3$S— 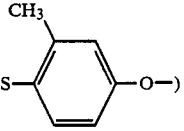 —O—) | CH$_3$ | CH$_3$ | |
| 34 | 3,5-Cl$_2$, 4-(Cl— 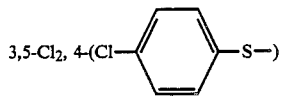 —S—) | CH$_3$ | CH$_3$ | |
| 35 | 3,5-(CH$_3$)$_2$, 4-(CH$_3$S— 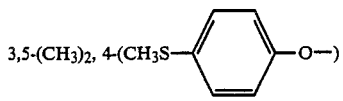 —O—) | CH$_3$ | CH$_3$ | |
| 36 | 3,5-Cl$_2$, 4-(CH$_3$S— 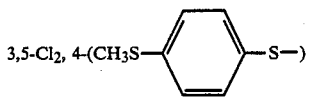 —S—) | CH$_3$ | CH$_3$ | |
| 37 | 3,5-Cl$_2$, 4-CH$_3$S— | CH$_3$ | CH$_3$ | |
| 38 | 3,5-(CF$_3$)$_2$ | CH$_3$ | CH$_3$ | 87 |
| 38a | 3,5-(CF$_3$)$_2$ | CH$_3$ | C$_2$H$_5$ | 91 |
| 38b | 3,5-Cl$_2$, 4-(CH$_3$SO$_2$— 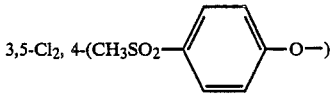 —O—) | CH$_2$— 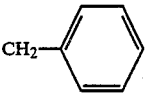 | CH$_3$ | 185 |
| 38c | " | CH$_3$CO | CH$_3$ | 233 |
| 38d | 3,5-(CF$_3$)$_2$ | CH$_3$ | Benzyl | 108 |

Example 39

2-[3,5-Dichloro-4-(4-methylsulfonylphenoxy)phenyl]-4-methylhexahydro-1,2,4-triazine-3,5-dione 1 g of 2-[3,5-dichloro-4-(4-methylsulfonylphenoxy)phenyl]hexahydro-1,2,4-triazine-3,5-dione was dissolved in 10 ml of dimethylformamide and, with exclusion of moisture, about 250 mg of a suspension of sodium hydride were added. After the evolution of gases was complete, 1 ml of methyl iodide was added, with stirring, and then the mixture was stirred at room temperature for a further 5 h. The reaction solution was poured onto water, and the precipitate was filtered off with suction and recrystallized from isopropanol, melting point 217° C.

NMR spectrum, 60 MHz, DMSO-d$_6$, TMS as internal standard, δ values in ppm: —N$^1$H—CH$_2$ 6.5 (tr, J=8 Hz), —N$^4$—CH$_3$ 3.1 (s) —N$^1$H—CH$_2$ 3.8 (d, J=8 Hz).

In an analogous procedure, the following compounds of the formula I additionally alkylated in the 4-position were obtained by alkylation from the particular 2-substituted hexahydro-1,2,4-triazine-3,5-diones:

| EXAMPLE NO. | $R^1$ | $R^2$ | $R^3$ | mp. °C. |
|---|---|---|---|---|
| 40 | 3,5-Cl$_2$, 4-(CH$_3$S— 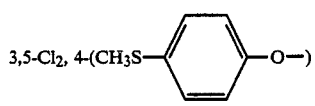 —O—) | H | CH$_3$ | 163 |
| 41 | 3,5-Cl$_2$, 4-(CH$_3$SO— 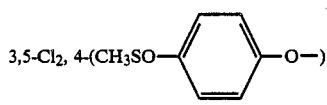 —O—) | H | CH$_3$ | |
| 42 | 3,5-Cl$_2$, 4-(CH$_3$SO$_2$— 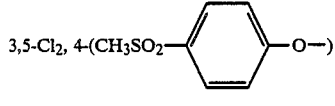 —O—) | H | C$_2$H$_5$ | 237 |
| 43 | 3,5-Cl$_2$, 4-(CH$_3$SO$_2$— 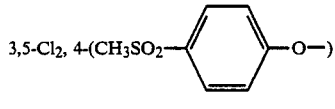 —O—) | H | C$_4$H$_9$ | 156 |

-continued

| EXAMPLE NO. | R¹ | R² | R³ | mp. °C |
|---|---|---|---|---|
| 44 | 3,5-Cl₂, 4-(CH₃SO₂—⟨phenyl⟩—O—) | H | CH₂—⟨phenyl⟩ | 197 |
| 45 | 3,5-Cl₂, 4-(CH₃S—⟨phenyl with CH₃⟩—O—) | H | CH₃ | |
| 46 | 3,5-Cl₂, 4-(Cl—⟨phenyl⟩—S—) | H | CH₃ | |
| 47 | 3,5-(CH₃)₂, 4-(CH₃S—⟨phenyl⟩—O—) | H | CH₃ | |
| 48 | 3,5-Cl₂, 4-(CH₃S—⟨phenyl⟩—S—) | H | CH₃ | |
| 49 | 3,5-Cl₂, 4-CH₃S— | H | CH₃ | |
| 50 | 3,5-(CF₃)₂ | H | CH₃ | 98 |
| 50a | 3,5-(CF₃)₂ | H | C₂H₅ | 118 |
| 50b | " | H | C₄H₉ | 80 |
| 50c | " | H | CH₂—⟨phenyl⟩ | 177 |

Preparation of the compounds of the formula II:

Example 51

2-[3,5-Dichloro-4-(4-methylsulfonylphenoxy)phenyl]-hexahydro-1,2,4-triazine-3,5-dione 10 g of 2-[3,5-dichloro-4-(methylsulfonylphenoxy)-phenyl]-1,2,4-triazine-3,5-(2H,4H)-dione were dissolved in 150 ml of hot glacial acetic acid, 10 g of zinc dust were added, and the mixture was heated to reflux for two hours. It was then filtered hot, and the zinc-containing residue was extracted by boiling three times with 50 ml of glacial acetic acid. The collected solutions were evaporated under reduced pressure, and water was added and filtration with suction was carried out. The remaining solid was recrystallized from methanol with the addition of active charcoal, melting point 240° C., decomposition.

NMR spectrum, 60 MHz, DMSO-d₆, TMS as internal standard, δ values in ppm: —N¹H—CH₂ 6.53 (tr, J=8 Hz), —N¹H—CH₂ 3.7 (d, J=8 Hz), CH₃SO₂— 3.2 (3).

Example 52

2-[3,5-Dichloro-4-(4-methylthiophenoxy)phenyl]hexahydro-1,2,4-triazine-3,5-dione 20 g of 2-[3,5-dichloro-4-(4-methylthiophenoxy)-phenyl]-1,2,4-triazine-3,5-(2H,4H)-dione were dissolved in 200 ml of hot glacial acetic acid. 25 g of tin(II) chloride.2H₂O, followed by 100 ml of concentrated hydrochloric acid, were added, and then the mixture was heated to reflux for four hours. After the mixture had been cooled, the product was filtered off with suction, washed to neutrality with water, and recrystallized from 2-methoxyethanol, melting point 239° C.

NMR spectrum, 60 MHz, DMSO-d₆, TMS as internal standard, δ values in ppm: —N¹H—CH₂ 6.53 (tr, J=8 Hz), —N¹H—CH₂, 3.7 (d, J=8 Hz), CH₃S— 2.45 (s).

B. BIOLOGICAL EXAMPLES

Coccidiostatic activity against *Eimeria tenella*

Chicks (4 to 50 animals/dose) with a body weight of 35 to 40 g were infected orally with *Eimeria tenella* by stomach tube. The positive control group (8 to 50 animals) was infected with the same dose as the medicated chicks (dose range 0.5 to 3.5×10⁵ sporulated oocysts/chick).

The text compounds of formula I were mixed with the feed having a usual commercial composition in a mixer. The feed was freely available to the animals throughout the study. For comparison purposes the study had also a negative control group, i.e. 8 to 50 non infected non medicated animals. The trial lasted about 10 days.

By applying the following compounds of Examples 1, 2, 3, 4, 5, 6, 7, 10, 11, 12, 14, 15, 16, 17, 18, 19, 20, 21a, 22, 23, 24, 25, 26, 31, 38a, 38b, 38c, 38d, 39, 40, 42, 43, 44, 50, 50a, 50b, 50c at a dosage rate of 100 ppm in the feed the chicks survived without any signs of coccidiosis, i.e. boody fecis, high oocyst production and intestine lesions was prevented.

We claim:
1. A compund of the formula I

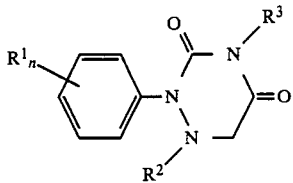

in which:
n is one, two or three and the individual substituents
R¹, independently of one another, each is
(a) hydrogen, F, Cl, Br, I, trifluoromethyl, alkyl having 1 to 6 carbon atoms, cycloalkyl having 3 to 6 carbon atoms, alkoxy, alkylthio, alkylsulfinyl or alkylsulfonyl, each having 1 to 6 carbon atoms in the alkyl radical, benzylthio, benzylsulfinyl or benzylsulfonyl, nitro, cyano, amino, alkylamino or dialkylamino, each having 1 to 12 carbon atoms in the alkyl radical, acylamino having 1 to 6 carbon atoms in the acyl radical, or
(b) a phenoxy, phenylthio, phenylsulfinyl, phenylsulfonyl, benzoyl, benzoylamino or anilino radical, each of which is substituted once, twice or three times by one of the substituents mentioned under (a);
R² is hydrogen, straight-chain or branched alkyl having 1 to 12 carbon atoms, cycloalkyl having 3 to 7 carbon atoms, benzyl which is unsubstituted or substituted by F, Cl, Br or ($C_1$-$C_4$)-alkyl, straight-chain or branched alkanoyl which has 1 to 12 carbon atoms and is unsubstituted or substituted once, twice or three times by F, Cl, Br, or benzoyl which is unsubstituted or substituted once or twice by F, Cl, Br or ($C_1$-$C_4$)-alkyl;
R³ is hydrogen, straight-chain or branched alkyl having 1 to 12 carbon atoms, cycloalkyl having 3 to 7 carbon atoms, or benzyl which is unsubstituted or substituted by F, Cl, Br or ($C_1$-$C_4$)-alkyl,
with the proviso that at least one of the radicals R² and R³ is not hydrogen, and their salts.

2. A compound as claimed in claim 1, wherein in formula I
n is two or three, and the individual substituents R¹, independently of one another, each is
(c) hydrogen, F, Cl, Br, CF₃, alkyl, alkoxy, alkylthio, alkylsulfinyl or alkylsulfonyl, each having 1 to 6 carbon atoms in the alkyl radical, or
(d) a phenoxy, phenylthio, phenylsulfinyl or phenylsulfonyl radical, each of which is substituted once or twice by one of the substituents mentioned under (c),
R² is hydrogen, straight-chain or branched alkyl or alkanoyl, each having 1 to 4 carbon atoms, cycloalkyl having 3 to 7 carbon atoms, benzyl or benzoyl which both are unsubstituted or substituted by F, Cl, Br or ($C_1$-$C_4$)-alkyl;
R³ is hydrogen, straight-chain or branched alkyl having 1 to 12 carbon atoms, cycloalkyl having 3 to 7 carbon atoms, or benzyl which is unsubstituted or substituted by F, Cl, Br or ($C_1$-$C_4$)-alkyl;
with the proviso that at least one of the radicals R² and R³ is not hydrogen.

3. A compound as claimed in claim 1, wherein in formula I
n is two or three, and the individual substituents
R¹, independently of one another, each is hydrogen, chlorine, trifluoromethyl, ($C_1$-$C_4$)-alkyl or phenoxy, which is substituted once or twice by alkylthio, alkylsulfinyl or alkylsulfonyl, each having 1 to 4 carbon atoms in the alkyl radical, or
R² is ($C_1$-$C_4$)alkyl, ($C_1$-$C_4$)alkanoyl or benzyl,
R³ is hydrogen, ($C_1$-$C_4$)alkyl or benzyl.

4. A compound as claimed in claim 3 wherein the phenyl radical in formula I is disubstituted in the 3,5-positions or trisubstituted in the 3,4,5-positions.

5. A veterinary composition which comprises a compound of formula I as claimed in claim 1, and a carrier therefor.

6. A method for combatting coccidiosis in animals which comprises administering to said animals an effective amount of a compound of formula I as claimed in claim 1.

* * * * *